United States Patent [19]

Goodson

[11] 4,175,326

[45] Nov. 27, 1979

[54] HOLLOW-FIBER DEVICES FOR AND A METHOD OF THE TREAMENT AND DIAGNOSIS OF ORAL DISEASES

[75] Inventor: Jo M. Goodson, Cambridge, Mass.

[73] Assignee: Forsyth Dental Infirmary for Children, Boston, Mass.

[21] Appl. No.: 845,587

[22] Filed: Oct. 26, 1977

[51] Int. Cl.² ............................................. A61C 19/06
[52] U.S. Cl. ......................................... 433/80; 424/14
[58] Field of Search ...................... 128/260, 222; 32/2, 32/40, 1; 424/14, 57, 55, 15-22; 132/89-91

[56] References Cited

U.S. PATENT DOCUMENTS

| 2,154,168 | 4/1939 | Klein et al. | 424/57 |
| 2,748,781 | 6/1956 | Collet | 132/93 |
| 3,942,539 | 3/1976 | Corliss | 132/91 |
| 3,967,618 | 7/1976 | Zaffaroni | 128/260 |
| 4,020,558 | 5/1977 | Cournut et al. | 32/40 R |

Primary Examiner—Robert Peshock
Attorney, Agent, or Firm—Richard P. Crowley

[57] ABSTRACT

Capillary hollow fibers containing therein therapeutic and indicator agents and a method of employing such fibers, which method comprises placing the agent-filled, hollow capillary fibers into the oral cavity, and particularly about, adjacent or in contact with the teeth, at or about those areas where treatment of a dental disease is desired, or where indication of the presence of an oral or a dental disease is suspected, whereby such agent permeates from such capillary-hollow-fiber treatment into the localized area to treat the disease or to serve as an indication of dental disease in the area.

19 Claims, 4 Drawing Figures

HOLLOW-FIBER DEVICES FOR AND A METHOD OF THE TREAMENT AND DIAGNOSIS OF ORAL DISEASES

BACKGROUND OF THE INVENTION

The treatment of dental diseases in the past has largely depended on surgical and restorative techniques. Compositions, such as toothpaste, gels, mouth washes and the like, containing fluorides and antibacterial agents have only met with some limited success and effectiveness, due in part to the very low time-retention rate of those agents after application in the oral cavity. In general drug therapy for dental diseases usually has been accomplished by the use of long-lasting tablets or capsules orally administered to the patient. For example, long-acting capsules or tablets containing odor-masking material or ingredients have been suggested for use in the oral cavity (see U.S. Pat. No. 3,911,099).

Other means for applying therapeutic agents to the oral cavity, and particularly to the teeth, have included the use of gels applied to teeth (see U.S. Pat. No. 3,679,360), the application of a plastic, hardenable mass to the teeth containing various agents (see U.S. Pat. No. 3,964,164), and the application of a foam-film device containing medication (see U.S. Pat. No. 3,844,286). In addition, fibers, as the carriers of therapeutic agents, also have been suggested, such as the impregnation of cotton twine with calcium hydroxyapatite for hemostasis of injured dental tissues (see U.S. Pat. No. 3,417,179); solid adsorbable fibers of polyglycolic acid with medicants incorporated therein (see U.S. Pat. No. 3,991,766); and impregnated dental floss for caries prevention (see U.S. Pat. No. 2,667,443). However, none of these suggested methods of therapeutic treatment has been wholly satisfactory nor widely adopted and accepted, due to a variety of causes and disadvantages associated with each technique.

The diagnosis of dental disease in current practice primarily relies on the use of dental radiographs and/or a manual probing and examination by a dentist of the oral cavity. Various indicators have been applied as oral devices to detect local changes in acidity and oxidation potential in the oral cavity for diagnostic purposes. Such prior diagnostic tests have been used to indicate a present condition, and have not provided any long-term indication of oral disease, or to monitor suspected oral disease.

SUMMARY OF THE INVENTION

My invention concerns polymeric, semipermeable, capillary hollow fibers which contain therein therapeutic and/or diagnostic agents, or combinations thereof, and a method for the treatment and diagnosis of dental diseases by the use of such agent-filled fibers.

My invention relates to a method for the localized treatment and diagnosis of dental disease by attachment of semipermeable hollow fibers to or about the tooth. In the treatment mode, an agent placed within the fiber is allowed to penetrate the semipermeable membrane at a controlled rate over a prolonged period of time in order to provide sustained localized therapy. In the diagnostic mode, an agent placed within the fiber is acted upon by a product of the disease process in order to provide an indication or a measure of localized disease activity of the region. The fibers are positioned between adjacent teeth or in the region surrounding the necks of teeth as being amenable to direct application of cylindrical fibers and as common sites of dental-caries activity. In particular, my invention relates to treatment and diagnosis of dental decay. Furthermore, the gum tissue surrounding the necks of the teeth is susceptible to inflammatory diseases termed periodontal disease or pyorrhea, and is likewise amenable to treatment or diagnosis by my hollow-fiber techniques.

In the treatment mode by semipermeable hollow fibers, therapeutic agents are administered directly to the locus of disease without suffering the dilution imposed by the blood and extracellular fluid compartments of the body. As a consequence of the reduced amount of drug necessary to render therapy, systemic reactions to the drug are dramatically decreased or eliminated, and the utility of drugs not generally administered for treatment of dental disease, because of their systemic effects, can be considered in therapy.

My invention also relates to an indicator or diagnostic system and method based on the qualitative or quantitative measurement and detection of respected diseases in the oral cavity, particularly localized disease about a tooth. For example, my method may be based on the erosion of tooth substances or a component of tooth substances as an indication of cariogenicity. My method may be employed in particular for the treatment of patients, and also for the assessment of the cariogenicity of food or food additives or the like, as well as for the diagnosis of disease in a human or an animal patient. For example, in one indicator system of dental-caries activity, a known amount of a powdered tooth enamel or other substance, or, for example, calcium or other salt hydroxyapatite crystals, may be introduced into the lumen of a capillary hollow fiber. The hollow fiber is then placed about the tooth, and, after suitable time, the hollow fiber is removed with its contents. The amount of calcified material remaining is then measured by any suitable procedure to determine the extent of dental-caries activity in the area.

The capillary hollow fibers useful in my invention may comprise a wide variety of semipermeable, polymeric materials, with, for example, a selection of a particular material and fiber depending upon the rate of permeation desired and other factors. Typically the hollow fibers employed should be composed of an inert, flexible, pharmaceutically acceptable material capable of being manufactured or formed into a loop or tied or otherwise interlaced into place about the tooth without breaking or being inordinately difficult in handling. Typically hollow fibers of my invention should not generally exceed about 500 microns in outside diameter; for example, from about 100 to 300 microns, with a wall thickness typically ranging from about as low as 1 micron; for example, from 5 to 100 microns. Capillary hollow fibers of such general type are commercially known and used (see, for example, U.S. Pat. No. 3,228,877, hereby incorporated by reference). The selected hollow fibers should have the ability to permit the desired gradual permeation of the particular treating or diagnostic agent over the desired time period, which may be as short as from 1 hour to 1 year or more; for example, 24 hours to 1 month. Typical hollow capillary fibers may be composed, for example, of synthetic or natural polymers, such as cellulosic polymers, and more particularly cellulosic esters and ethers, as well as a variety of other inert polymeric materials like nylon, polyglycolic polymers and copolymers, etc.

The preferred hollow fibers made of cellulose acetate or similar material are manufactured and are commercially available which have an outside diameter of approximately 250 microns, an inside diameter of approximately 200 microns and an internal volume of approximately 0.3 microliter per linear centimeter. The hollow-fiber walls are made semipermeable to materials of different molecular sizes by controlling the degree of cross-linkage achieved within the polymer, or by the size of the pores during the manufacturing process. My invention, in its preferred embodiment, concerns utilization of fibers of this type for the treatment and diagnosis of oral diseases.

In the treatment or the diagnostic mode, the agent-filled hollow fibers are placed about or adjacent the teeth to be treated or diagnosed. The fibers may be inserted in short lengths between the teeth, or preformed into loops of a size which will generally fit snugly over the tooth and rest on the oral tissue surrounding and about the root of the tooth, or otherwise be placed over the tooth or between the teeth. My flexible, agent-filled, hollow fibers also may be employed by wrapping the fiber about the tooth and tying the fiber, or by interlacing the fiber between one or more teeth, or otherwise by placing the fiber into the localized area to be treated or diagnosed. Typically the hollow fiber should be positioned such as to be retained in place during normal functioning of the patient, and should be such as to be removed easily and rapidly. The hollow fiber may be retained in the oral cavity for as long as required or needed in either the diagnostic or the treating mode, depending upon the permeation rate from the fiber or of the particular agent.

It is recognized that other materials, besides the active therapeutic and treatment agents, may be incorporated into the luminal fiber together with such active materials, such as the use of liquid inert carriers, solvents, suspending agents, surfactants, viscosity-control agents, antibacterial agents, buffers, diluents, complexing agents, and other pharmaceutically acceptable materials which may be employed to solubilize or stabilize the materials in the lumen, or to control the rate of permeation or the action of the materials after permeation.

In the treatment mode, various therapeutic agents are introduced into the lumen of the fiber which is tied around the tooth at selected sites. The therapeutic agent diffuses out of the fiber at a rate controlled by the permeability of the fiber wall and the internal concentration of the agent to be delivered. The agent achieves a therapeutically active concentration in the immediate vicinity of the fiber (tooth and localized tissue) and is diluted to an inactive level as it escapes into the saliva.

A wide variety of therapeutic agents may be used in my invention. Some therapeutic agents, which are amenable to delivery by this means and are potentially of value for oral therapy, include, but are not limited to: antibacterial agents, such as iodine or chlorohexidine; antibiotics, such as tetracycline or penicillin; antifungal agents, such as nystatin; antiinflammatory agents, such as indomethacin or hydrocortisone; immune-supressive or stimulatory agents, such as methotrexate or levamasol; fluorides, such as calcium, sodium, stannous or amine fluoride; dentinal desensitizing agents, such as strontium chloride or sodium fluoride; recalcification solutions, such as saturated calcium phosphate; odor-masking or inhibiting agents, such as peppermint oil or chlorophyll; or oxygen-releasing agents, such as urea peroxide.

Several modified versions of my invention include the use of hollow fibers which are either wholly or in part made of biodegradable substances; for example, polyglycolic acid and various copolymers, which disintegrate or are body-absorbable after the agent is delivered. Fiber construction with intermittent occlusions prevent leakage from cut ends. Inclusion of nondialyzable binding substances with drugs, such as polyvinyl pyrrolidone, with iodine or complexing agents, such as calcium with tetracycline or procaine with penicillin to alter the release from hollow fibers, are effective in delaying drug release and constitute methods for regulating the rate at which agents are delivered.

In the diagnostic mode, various indicator materials are introduced into the lumen of the fiber to be acted upon by the local dental-disease process. The fiber provides mechanical support for the indicator material at sites between and around teeth, and allows access to substances eminating from these areas by diffusion through the hollow-fiber wall. The indicator substance provides diagnostic information by undergoing chemical reaction with the products elaborated by the localized disease process. Indicators applicable to this purpose include, but are not limited to, the following: acid-base indicators, such as methyl orange; oxidation-reduction indicators, such as methylene blue; indicators of corrosive action on tooth substances, such as the loss of hollow-fiber-incorporated ground tooth enamel, calcium salts or calcium hydroxyapatite; or indicators of proteolytic action eminating from the gums consisting of proteinaceous materials capable of being digested by specific enzymes, such as collagen or fluorescein-labeled hemoglobin.

The therapeutic treatment agents may be introduced into the lumen of the hollow fibers by a variety of techniques, either during manufacture or thereafter. Such techniques would include, but not be limited to: aspiration of a solution containing the active ingredients into the lumen; pumping of the solution into the lumen; or permeation or injection of solutions and agents into the lumen. After such introduction of the agents into the lumen to fill or fill partially the lumen, depending upon the amount of material to be dispensed over the time period, the hollow capillary fiber may be employed with open ends, or the ends may be occluded, such as by heat-sealing or by occluding polymers, or other techniques.

My invention will be described for the purpose of illustration only in connection with certain preferred embodiments, and it is recognized that certain changes and modifications may be made by a person skilled in the art, which changes and modifications are within the spirit and scope of my invention.

DESCRIPTION OF THE EMBODIMENTS

EXAMPLE 1

Figure 1:
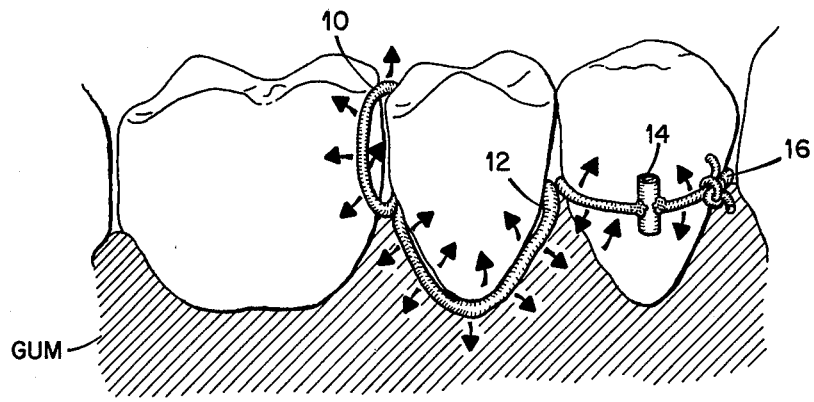
FIG. 1 is a schematic illustration showing the use of my hollow fiber about the teeth of a patient.

A length of cellulose-acetate hollow fiber, with a stated molecular-weight cutoff of 200 daltons, was cemented into the lumen of a 26-gage hypodermic needle. A saturated solution of tetracycline hydrochloride in water was pumped into the hollow fiber by means of a peristaltic pump with silicone-rubber-pump tubing. The needle was attached by a standard luer fitting to Teflon tubing which fit the inner bore of the silicone-pump tubing. After filling the fiber with the suspension, the distal end was occluded and the pumping maintained. The solvent (water), being smaller than a tetracycline molecule, more readily permeated the fiber wall. After a time, the fiber became completely filled with tetracycline. The average content of fibers so constructed was 224 micrograms per linear centimeter, 75% of the maximum theoretical content of 300 micrograms per centimeter.

The release of tetracycline from a test segment of this fiber into distilled water was measured spectrophotometrically and was found to persist for 3 to 6 hours, with the highest concentration being delivered after 30 minutes.

Tetracycline-filled fibers thus constructed were tied around the necks of teeth of a patient afflicted with periodontal disease, and were pressed used the margin of the gum tissue. Prior microbiological diagnosis revealed a preponderance of large spirochetes. A comparison of spirochete counts before and after placement of the fiber revealed that the spirochetes had been eliminated completely by a single application of tetracycline-filled fibers. Concomitantly signs of inflammation in the treated area disappeared. Thus a beneficial therapeutic result followed the placement of tetracycline-filled fibers about the necks of teeth. Other antibiotic drugs effective against Streptococcus mutans and other microorganisms also may be used.

EXAMPLE 2

A length of cellulose-acetate hollow fiber was prepared as described in the preceding example. Powdered polyvinyl pyrrolidone (viscosity-control agents) was added to a saturated solution of iodine in an alcohol (ethanol) to form a thick solution. After filling the fiber with this solution, it was dried and the needle was removed.

The release of iodine from a test segment of this fiber was studied spectrophotometrically, and was found to persist for more than 24 hours, with the highest concentrations being delivered during the first hour.

Iodine-filled, flexible fibers thus constructed were tied around the necks of teeth of a patient afflicted with periodontal disease. A comparison of bacterial counts before and after placement of the fiber revealed a reduction in numbers, and concomitantly signs of inflammation decreased. Thus a beneficial therapeutic result resulted from the placement of iodine-filled fibers about the necks of teeth.

EXAMPLE 3

A fiber of the same construction as previously described was filled with a saturated solution of sodium fluoride. After filling, the luer fitting connecting the fiber was removed and a solution of 0.1 molar calcium chloride was pumped in. With the entrance of a stream containing calcium, insoluble calcium fluoride precipitated, filling the inner lumen of the fiber.

A fiber thus constructed was applied about the neck of a tooth exhibiting dentinal sensitivity. Following a single application, the sensitivity was decreased, indicating that fluoride release had occurred and that local therapeutic activity had resulted.

EXAMPLE 4

Fibers of the type described were filled with a solution from which calcium hydroxyapatite was precipitated by solvent evaporation. Fibers were cut in lengths of 2 mm and were sealed at either end with silicone cement. A 2-millimeter fiber segment was coated with a drop of silicone cement, and a length of suture material was lowered in a controlled manner to contact the coated fiber. After contact had been established, the cement was allowed to dry to provide a length of suture material adhesively secured at one end to the middle of the fiber segment. The suture material, being flexible and pharmaceutically acceptable, provides a means of securing the agent-containing hollow fiber against the tooth or gum surface by tying the fiber about the tooth. This technique is desirable where the hollow-fiber material does not have the flexibility or strength to be tied, itself, directly to the tooth. String, dental floss and other fibrous suture-like materials or other means, such as adhesives, clamps, etc., may be employed to retain or hold the agent-containing fiber to the tooth or gum surface. Also in the treatment of some dental diseases, such as periodontal disease, the agent-containing hollow fiber may be inserted or implanted beneath the gum surface, such as tacked beneath the gum surface adjacent the tooth surface, for treatment or diagnosis of the area.

Fiber segments so prepared were tied between the teeth of a patient suspected of having active dental caries. The fibers were worn overnight and were analyzed the next day for the residual calcium content. Analysis indicated a loss of more than 50% of the calcium contained in the fibers. Since fibers placed on the teeth of patients without dental caries lose no more than 10% on an overnight application, and the variation between fibers produced is no greater than 5%, it was concluded that the loss of calcium from precipitated calcium hydroxyapatite was the result of dental-caries activity. Furthermore, the loss of calcium in this application acted as a diagnostic indicator of dental-caries activity.

In reference to the drawings, FIG. 1 shows therapeutic-agent- and diagnostic-agent-filled capillary hollow fibers, wherein a small, looped, hollow fiber 10, containing a solution of a treating or diagnostic agent, is placed between the teeth, and also wherein a preformed hollow-fiber loop 12 has been placed over the tooth and rests on or adjacent the oral tissue about the root of the tooth. Also an agent-filled hollow fiber 14 is tied with suture material 16 around a tooth. In all embodiments, as illustrated, the therapeutic or treatment agent is permeating from the lumen of the hollow fiber and through the walls thereof and to the tooth surface or to the tooth surface and/or the surrounding gum tissue of the tooth, to provide treatment or diagnostic detection.

Figure 2:
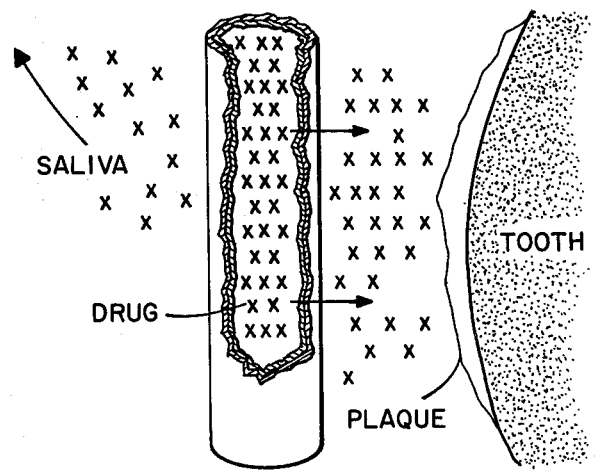
FIG. 2 is an enlarged schematic illustration of the localized, intraoral delivery of a drug by the use of a hollow fiber to a tooth.

FIG. 2 is a generally schematic enlarged illustration of a localized, intraoral drug delivery of a drug contained within the lumen of a large fiber, and the passage of the drug illustrated through the wall of the fiber and into the saliva to treat effectively the tissue or impose on the plaque surrounding the tooth.

Figure 3:
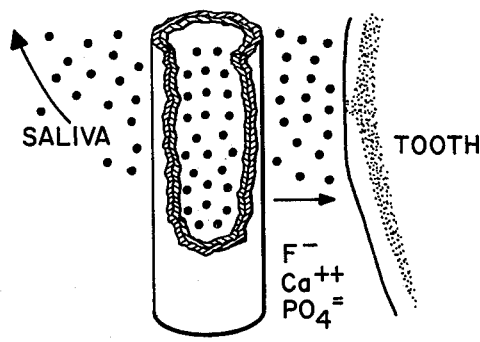
FIG. 3 is an enlarged schematic illustration of the delivery of fluoride and/or calcium solution to a tooth surface by the use of a hollow fiber.

FIG. 3 is an illustration illustrating the delivery of fluoride and/or calcification solutions containing fluoride, calcium and phosphate from the interior lumen of the hollow fiber adjacent the teeth to the tooth surface for the treatment and prevention of dental caries.

Figure 4:
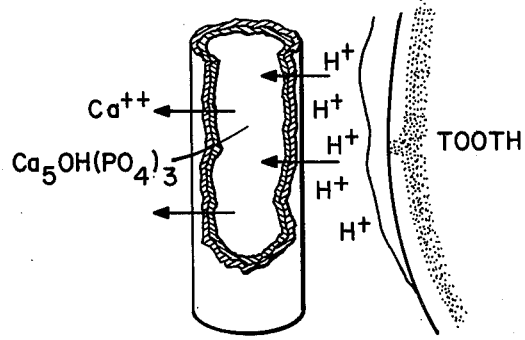
FIG. 4 is an enlarged schematic illustration of the use of hollow fibers in the detection of dental disease about a tooth.

FIG. 4 schematically illustrates the employment of hollow fibers, as in Example 4, to detect the measurement of dental caries in a tooth and the amount of caries activity by the reduction of a hydroxyapatite salt of a known amount contained within the hollow fiber.

What I claim is:

1. A capillary hollow fiber suitable for diagnostic use in the detection of a dental disease in the oral cavity of a patient, which fiber comprises a flexible, semipermeable, polymeric material having an outside diameter of not greater than 500 microns and a wall thickness of from about 1 to 100 microns, the lumen of the fiber containing a known quantity of an indicator-diagnostic agent wherein the indicator agent is selected from the group of acid-base indicator agents, oxidation-reduction indicators, tooth-corrosive-action indicators and proteinaceous proteolytic-action indicators which provides diagnostic information by undergoing chemical reaction with the products elaborated by the localized disease process in the oral cavity whose diagnosis is desired, the indicator agent capable of diffusing out of the fiber at a rate controlled by the permeability of the fiber.

2. The hollow fiber of claim 1 wherein the fiber has an outside diameter of from about 100 to 300 microns, and a wall thickness of from about 5 to 100 microns.

3. The hollow fiber of claim 1, which hollow fiber is a cellulose-acetate fiber.

4. The hollow fiber of claim 1 wherein the hollow fiber is preformed into a generally loop shape of sufficient size to be slipped over the crown of a tooth, and to rest about and be generally in contact with the tooth dental tissue surface.

5. The hollow fiber of claim 1, which fiber contains therein a known quantity of a calcium hydroxyapatite.

6. The hollow fiber of claim 1 wherein the hollow fiber is adhesively secured to a flexible, pharmaceutically acceptable string element, which string element is adapted to be tied about the tooth of a patient and to retain the hollow fiber against the tooth.

7. The hollow fiber of claim 1 wherein the ends of the hollow fiber are occluded.

8. The hollow fiber of claim 1 which is in a preformed loop of sufficient size for the loop to be inserted between adjacent teeth in the mouth of a user.

9. The hollow fiber of claim 1 which includes in the lumen a known quantity of precipitated hydroxyapatite crystals and wherein the ends of the fiber are occluded.

10. The hollow fiber of claim 1 which includes a short length of fiber adhesively secured to a fibrous, flexible suture-like material, whereby the fibrous material may be tied about a tooth and the short fiber length placed in direct contact with a tooth surface in the oral cavity.

11. A method for the localized diagnostic detection of diseases in the oral cavity, which method comprises:

(a) placing a semipermeable, polymeric, capillary hollow fiber, which contains a known quantity of a diagnostic-indicator agent within the lumen of the fiber, about or adjacent the tooth in the oral cavity where a dental or oral disease is suspected, the hollow fiber composed of a polymeric material which is permeable to the diagnostic agent therein, the indicator agent providing diagnostic information by chemical reaction with the products elaborated by the localized disease process in the oral cavity; and, thereafter, (b) analyzing, after a designated period of time, the change in the nature or quantity of the diagnostic agent in the lumen as a measure of the dental disease in the localized area.

12. The method of claim 11 wherein the hollow fiber comprises a cellulose-acetate hollow fiber.

13. The method of claim 11 wherein the capillary hollow fiber is formed into a loop, and the step of placing includes slipping the preformed loop containing the therapeutic drug over the tooth and peripherally about the tooth.

14. The method of claim 11 wherein the step of placing includes placing a preformed loop of the hollow fiber adjacent and in between two teeth.

15. The method of claim 11 which includes placing the hollow fiber about the tooth by tying a hollow fiber about the periphery of the tooth.

16. The method of claim 11 which includes placing the hollow fiber adjacent or between the gum and the tooth to be treated.

17. The method of claim 11 wherein the diagnostic agent comprises calcium hydroxyapatite.

18. The method of claim 11 wherein the diagnostic agent comprises a known, measured amount of calcium hydroxyapatite within the lumen, and wherein the hollow fiber is removed and the amount of remaining calcium hydroxyapatite in the lumen is determined after a designated period of time to determine the degree of dental cariogenicity of the localized tooth area.

19. The method of claim 11 wherein the indicator agent is selected from the group of acid-base indicator agents, oxidation-reduction indicators, tooth-corrosive-action indicators and proteinaceous proteolytic-action indicators.

* * * * *